(12) United States Patent
Karalekas

(10) Patent No.: US 11,925,388 B1
(45) Date of Patent: Mar. 12, 2024

(54) SYSTEMS AND DEVICES FOR FACILITATING CONCEPTION

(71) Applicant: CKNS, LLC, Suffield, CT (US)

(72) Inventor: Camille Karalekas, Suffield, CT (US)

( * ) Notice: Subject to any disclaimer, the term of this patent is extended or adjusted under 35 U.S.C. 154(b) by 0 days.

(21) Appl. No.: 18/135,406

(22) Filed: Apr. 17, 2023

(51) Int. Cl.
*A61B 17/425* (2006.01)

(52) U.S. Cl.
CPC .................................. *A61B 17/425* (2013.01)

(58) Field of Classification Search
CPC ..................................................... A61B 17/425
See application file for complete search history.

(56) References Cited

U.S. PATENT DOCUMENTS

| | | | | |
|---|---|---|---|---|
| 6,264,638 B1 * | 7/2001 | Contente | ............. | A61M 31/002 604/285 |
| 11,452,547 B2 | 9/2022 | Stal | | |
| 2004/0089312 A1 * | 5/2004 | Jordan | ...................... | A61F 6/08 128/887 |
| 2013/0267769 A1 * | 10/2013 | La Vean | ..................... | A61F 6/08 600/33 |
| 2018/0014854 A1 * | 1/2018 | Souther | ................... | A61B 17/43 |
| 2018/0199874 A1 * | 7/2018 | Hwang | ............... | A61B 10/0045 |
| 2019/0336167 A1 * | 11/2019 | La Vean | ............... | A61B 17/425 |
| 2020/0046572 A1 | 2/2020 | Hwang | | |
| 2021/0069009 A1 * | 3/2021 | Im | ......................... | A61F 5/4553 |
| 2021/0267640 A1 * | 9/2021 | Stal | ........................ | A61B 17/43 |

FOREIGN PATENT DOCUMENTS

| | | | | | |
|---|---|---|---|---|---|
| BR | 202019005049 U2 | * | 9/2020 | | |
| BR | 202019012553 U2 | * | 12/2020 | ............. | A61F 5/451 |
| CA | 2278758 A1 | * | 8/1998 | | |
| CN | 111803256 A | * | 10/2020 | ............... | A61F 5/00 |
| WO | WO-2017015767 A1 | * | 2/2017 | | |
| WO | WO-2022225070 A1 | * | 10/2022 | ........... | A61B 5/0002 |
| WO | WO-2023034401 A1 | * | 3/2023 | | |

OTHER PUBLICATIONS

Brown, M. (Sep. 21, 2018). Some people are using menstrual cups to get pregnant faster and it just might work. Parents. https://www.parents.com/getting-pregnant/trying-to-conceive/using-menstrual-cups-to-get-pregnant-ttc/ (Year: 2018).*
Talia Shirazi, P. (Jan. 19, 2023). Menstrual Cups and soft cups for conception: Do they work?. Ro. https://ro.co/health-guide/menstrual-cups-and-soft-cups-conception/ (Year: 2023).*

* cited by examiner

*Primary Examiner* — Christine H Matthews
*Assistant Examiner* — Marc D. Honrath
(74) *Attorney, Agent, or Firm* — Wilson Dutra, PLLC; Camille A. Wilson

(57) ABSTRACT

The present disclosure provides for systems, methods, and devices for facilitating conception. According to the present disclosure, a conception facilitating device may comprise at least one frame and at least one base. In some embodiments, the at least one frame may be configured to at least partially surround the at least one base. In some aspects, the conception facilitating device may be configured to be insertable into a vaginal canal. The conception facilitating device may be comfortably inserted into a vaginal canal for a period of time, which may increase the possibility of conception.

14 Claims, 10 Drawing Sheets

900

SYSTEMS AND DEVICES FOR FACILITATING CONCEPTION

BACKGROUND

Getting pregnant is not easy. In fact, there is roughly only a 1 in 5 chance that a couple trying to conceive will become pregnant in a given month. There are recommendations for women trying to conceive like finding their fertility window, modifying one's diet, exercising, avoiding alcohol consumption, and more. Still, even when following these methods, one may struggle to become pregnant.

These difficulties in conceiving often lead to couples trying less effective and safe practices. One at-home pregnancy method is using a turkey baster to inject semen close to the cervix. However, the effectiveness of this pregnancy technique is lower than regular intercourse. A similar trend is revealed when looking at practices such as laying down after intercourse. There is no evidence that these practices increase a woman's chance at getting pregnant, rather some of them yield worse results.

To date, there is not any at-home, easy to access items and methods for getting pregnant available to women that are safe and reliable. Instead, many women who struggle with pregnancy struggle with the option to pay thousands, if not tens of thousands of dollars on practices such as in vitro fertilization, medications to induce ovulation, other doctor-prescribed medications, or even a surrogate.

The difficulty for accessible pregnancy devices is discovering options that women and doctors are comfortable with. There needs to be a method of getting pregnant that is inexpensive, safe, and reliable. Until such a product is developed, women will continue to practice unsafe, unreliable methods of getting pregnant or will struggle with the decision to pay large sums of money to use the methods that are recommended by doctors.

SUMMARY OF THE DISCLOSURE

What is needed are systems and devices for facilitating conception. People are in need of a convenient and inexpensive way to increase the possibility of conception. Current conception assisting insertion methods may include suctioning directly to the cervix. Therefore, a more comfortable conception facilitating device would increase the amount of time the user can have the conception facilitating device inserted, and keeping the ejaculate in constant contact with the vaginal canal may increase the possibility of conception.

The present disclosure provides generally for systems and devices for facilitating conception. According to the present disclosure, a conception facilitating device may comprise at least one frame, wherein the at least one frame may comprise at least one wall, and at least one base, wherein the at least one base may comprise at least one outer surface and at least one inner surface. In some embodiments, the at least one frame may be configured to at least partially surround the at least one base. In some aspects, the conception facilitating device may be insertable into a vaginal canal through the vaginal opening, wherein when the conception facilitating device is inserted into the vaginal canal through the vaginal opening, at least one portion of the outer surface of the at least one base may be directly adjacent to at least a portion of the vaginal canal. In some embodiments, the conception facilitating device may be configured to block at least an amount of ejaculate from exiting a vaginal opening from the vaginal canal.

In some embodiments, a method for facilitating conception may comprise the step of obtaining a conception facilitating device, wherein a conception facilitating device may comprise at least one frame and at least one base. In some aspects, the at least one frame may comprise at least one wall, and the at least one base may comprise at least one outer surface and at least one inner surface. In some embodiments, the conception facilitating device may be configured to block at least an amount of ejaculate from exiting a vaginal opening. In some embodiments, the method may comprise the step of inserting the conception facilitating device into a vaginal canal through the vaginal opening so that it may be positioned relatively close to the vaginal opening. In some aspects, the method may comprise the step of removing the conception facilitating device from the vaginal canal. In some embodiments, the method may further comprise removing the conception facilitating device after a predetermined amount of time. As a non-limiting example, the conception facilitating device may be inserted into the vaginal canal after intercourse. As an additional non-limiting example, the method for facilitating conception may further comprise delivering at least an amount of ejaculate to the at least one base of the conception facilitating device before insertion into the vaginal canal, wherein the conception facilitating device may be inserted into the vaginal canal with the at least an amount of ejaculate.

By way of example and not limitation, the conception facilitating device may comprise at least one receptacle located relatively close to the vaginal opening, wherein the at least one receptacle may be configured to project at least an amount of ejaculate in the direction of a user's cervix. In some aspects, this increase in time of contact between the ejaculate and a user may increase the possibility of conception. In some embodiments, the at least one receptacle may be configured to transition from a first position to a second position wherein the at least one receptacle comprises a material that structurally biases the at least one receptacle to the second position. In some aspects, this decrease in the distance between the ejaculate and a user's cervix may increase the possibility of conception.

In some embodiments, the conception facilitating device may be configured to comprise at least one cover, wherein the at least one cover may be configured to enclose at least a portion of the at least one base. In some embodiments, the at least one cover may be dissolvable. By way of example and not limitation, the at least one cover may be configured to dissolve after a period of time or upon the happening of an event, such as being inserted into the vaginal opening. This may allow users to store at least an amount of ejaculate within the conception facilitating device for a period of time before insertion. This may be useful for same sex couples who may need to store the ejaculate for a period of time.

In some aspects, the conception facilitating device may comprise at least one transmitter and at least one sensor, wherein the at least one transmitter and at least one sensor may be configured to interface with at least one external computing device In some embodiments, the at least one sensor may be configured to collect at least one datum, wherein the at least one datum may comprise time, pH, moisture levels, or any other health factor that may contribute to the health and wellness of the user. This may allow for the conception facilitating device to gather information that could potentially instruct the user on best practices for conceiving, which can be a long and difficult process. For example, the conception facilitating device may gather data that indicates the best time for a user to conceive.

In some aspects, the at least one database may be configured to store the at least one datum collected from the at least one sensor. This may allow for the collection of data overtime, which may be analyzed to give the instructions to the user for facilitating conception. In some aspects, the at least one transmitter may transmit the at least one datum gathered from the at least one sensor to at least one external computing device. In some aspects, the at least one external device computing device may comprise a mobile device, wherein a user can access data gathered from the conception facilitating device and the at external computing device may analyze the data to give the user information about facilitating conception. This may allow a user to make a decision that may aid in facilitating conception, and a user may use this data to consult with their physician about their health or their attempts to conceive.

BRIEF DESCRIPTION OF THE DRAWINGS

The accompanying drawings that are incorporated in and constitute a part of this specification illustrate several embodiments of the disclosure and, together with the description, serve to explain the principles of the disclosure.

DETAILED DESCRIPTION

The present disclosure provides generally for systems and devices for facilitating conception. According to the present disclosure, a conception facilitating device may comprise at least one frame, wherein the at least one frame may comprise at least one wall, and at least one base, wherein the at least one base may comprise at least one outer surface and at least one inner surface. In some embodiments, the at least one frame may be configured to at least partially surround the at least one base. In some aspects, the conception facilitating device may be insertable into a vaginal canal through the vaginal opening, wherein when the conception facilitating device is inserted into the vaginal canal through the vaginal opening, at least one portion of the outer surface of the at least one base may be directly adjacent to at least a portion of the vaginal canal. In some embodiments, the conception facilitating device may be configured to block at least an amount of ejaculate from exiting a vaginal opening from the vaginal canal.

In some embodiments, a method for facilitating conception may comprise the step of obtaining a conception facilitating device configured wherein a conception facilitating device may comprise at least one frame and at least one base. In some aspects, the at least one frame may comprise at least one wall, and the at least one base may comprise at least one outer surface and at least one inner surface. In some embodiments, the conception facilitating device may be configured to block at least an amount of ejaculate from exiting a vaginal opening. In some embodiments, the method may comprise the step of inserting the conception facilitating device into a vaginal canal through the vaginal opening so that it is positioned relatively close to the vaginal opening. In some aspects, the method may comprise the step of removing the conception facilitating device from the vaginal canal.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Conception Facilitating Device: as used herein refers to any device configured to at least partially limit the exiting of at least an amount of ejaculate from a vaginal canal.

Receptacle: as used herein refers to any element of a conception facilitating device that may hold at least an amount of ejaculate. By way of example and not limitation, a receptacle may comprise an indentation, depression, cavity, or crevice in at least one base of a conception facilitating device.

Figure 1A:
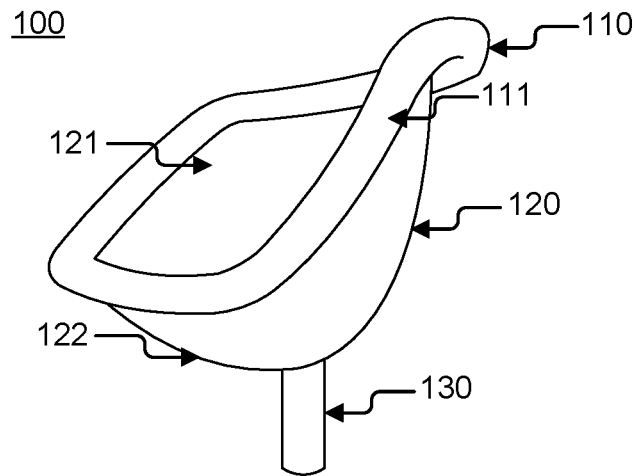
FIG. 1A illustrates an exemplary conception facilitating device, in accordance with some embodiments of the present disclosure.
Figure 1B:
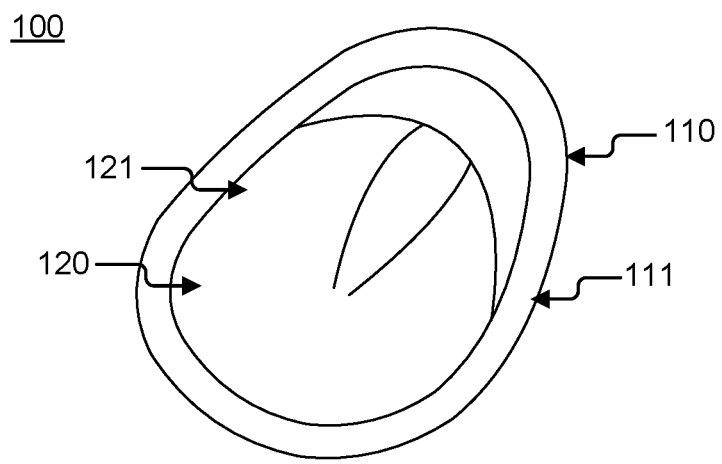
FIG. 1B illustrates a top view of an exemplary conception facilitating device, in accordance with some embodiments of the present disclosure.
Figure 1C:
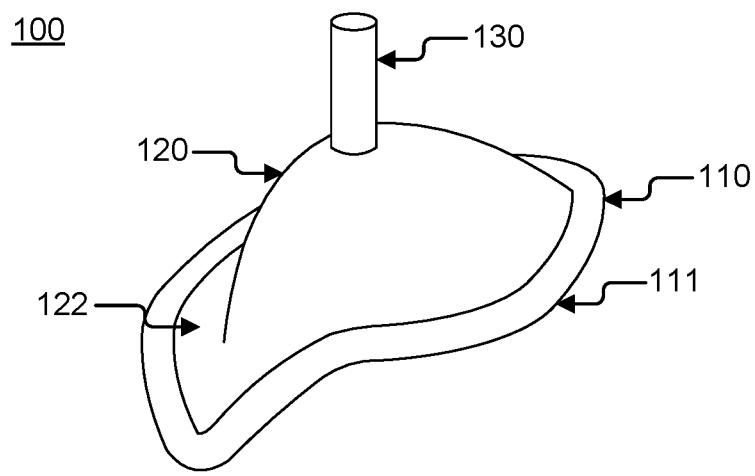
FIG. 1C illustrates an exemplary conception facilitating device, in accordance with some embodiments of the present disclosure.

Referring now to FIGS. 1A, 1B, and 1C, an exemplary conception facilitating device 100, in accordance with some embodiments of the present disclosure, is illustrated. In some aspects, a conception facilitating device may comprise at least one frame 110 and at least one base 120, wherein the at least one frame 110 may comprise at least one wall 111, and at least one base 120, wherein the at least one base may comprise at least one outer surface 122 and at least one inner surface 121 In some embodiments, the at least one frame 110 may be configured to at least partially surround the at least one base 120.

By way of example and not limitation, the conception facilitating device 100 may increase the likelihood of conception for a user when the at least one base 120 blocks at least an amount of ejaculate from existing the vaginal canal through the vaginal opening. In some embodiments, the conception facilitating device may comprise at least one protruding member 130, wherein the at least one protruding member 130 may be configured to facilitate the insertion and removal of the conception facilitating device 100, and wherein the at least protruding member 130 may be at least partially attached to the at least one base 120. By way of example and not limitation, the conception facilitating device 100 may comprise a base 120 completely surrounded by a frame 110.

In some embodiments, the at least one frame 110 and the at least one base 120 may be configured in a shape to enhance comfort to the user when in use, which may be a circular or non-circular shape. As a non-limiting example, the at least one frame 110 and the at least base 120 may be shaped in a non-circular shape, such as an asymmetrical shape with distinct curvatures. In some aspects, the non-circular shape may be configured to match the shape of the vaginal canal, and this may increase the amount of time a user may comfortably use the conception facilitating device 100.

As an illustrative example, the at least one frame 110 and the at least one base 120 may comprise an upper portion and a lower portion, wherein the higher portion may hold the conception facilitating device 100 in place in the vaginal canal. In some aspects, this may aid the conception facilitating device 100 in blocking at least an amount of ejaculate from exiting the vaginal canal because the conception facilitating device 100 does not move from its secured place in the vaginal canal. In some aspects, the conception facilitating device 100 may be configured to be a customizable shape to fit an individual user. As an illustrative example, the conception facilitating device 100 may comprise one or more materials that mold to the shape of a user's vaginal canal. As another an illustrative example, a user may provide specifications for the shape of the at least one frame and the at least one base to be used during the manufacturing process. As a non-limiting example, the manufacturing process may comprise additive manufacturing. As an illustrative example, a user may receive a conception facilitating device 100 that fits in accordance with these specifications.

In some aspects, the conception facilitating device 100 may comprise a flexible material, including but not limited to, elastic materials or a structurally resilient material. By way of example and not limitation, a flexible material may comprise one or more compositions of rubber, plastic, silicone, or any polymer-based material, as non-limiting examples. In some aspects, the conception facilitating device 100 may be configured such that a user may manipulate the structure of the device when inserting the conception facilitating device 100 into the vaginal canal through the vaginal opening As an illustrative example, a user may squeeze or fold the conception facilitating device 100 into a more compact shape before insertion, and after insertion, the conception facilitation device 100 may return to its original shape.

In some aspects, a user may squeeze and fold the conception facilitating device 100 into a smaller shape while it is inserted, and a user may squeeze or fold the conception facilitating device 100 to facilitate removal from the vaginal canal. As a non-limiting example, the conception facilitating device may comprise a reusable material, wherein a user may clean and reuse the conception facilitating device 100 a number of times. In some aspects, the reuse of the conception facilitating device 100 may allow a user to use the device more often, which may allow for an increased likelihood of conception.

In some aspects, the base 120 of the conception facilitating device 100 may be configured to hold at least one medication. In some non-limiting exemplary embodiments, a user may insert the conception facilitating device 100 with an amount of medication contained within the base 120, and the medication may provide at least one health benefit to the user. By way of example and not limitation, a user may use the conception facilitating device 100 to apply medication that may aid in increasing the likelihood of conception.

In some aspects, the conception facilitating device 100 may be used by a physician for implementing one or more medical procedures. For example, during a colposcopy, a common medical procedure, a physician may use the conception facilitating device 100 to apply an acetic acid solution to the cervix. In some implementations, a physician may at least partially fill the base 120 of the conception facilitating device 100 with the acetic acid solution and insert the conception facilitating device 100 into the vaginal canal. The conception facilitating device 100 may increase the efficiency of the application of the solution and decrease the likelihood the solution may spill onto the patient, which may be uncomfortable.

In some embodiments, the at least one protruding member 130 may be configured such that a user may grab the protruding member to move the conception facilitating device 100. In some embodiments, the at least one protruding member 130 may comprise a rigid material, such as plastic, metal, or rubber, as non-limiting examples. In some aspects, the rigid material of the at least one protruding member 130 may facilitate insertion and removal of the conception facilitating device 100.

As an illustrative example, a user may pinch the at least one protruding member 130 to pull the conception facilitating device 100 downward out of the vaginal canal. In some embodiments, the at least one protruding member 130 may comprise different shapes that may facilitate easier removal of the conception facilitating device 100, such as a cylinder-like member, a string-like member, a hook-like member, or a sphere-like member, as non-limiting examples.

Figure 2A:
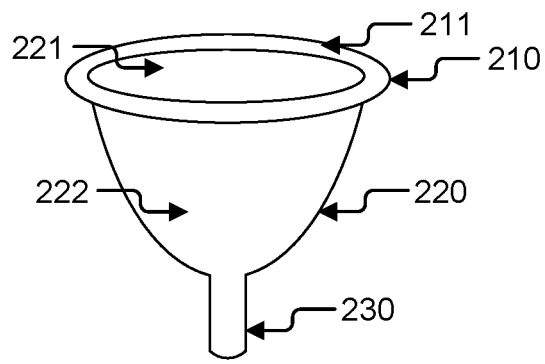
FIG. 2A illustrates an exemplary conception facilitating device, in accordance with some embodiments of the present disclosure.
Figure 2B:
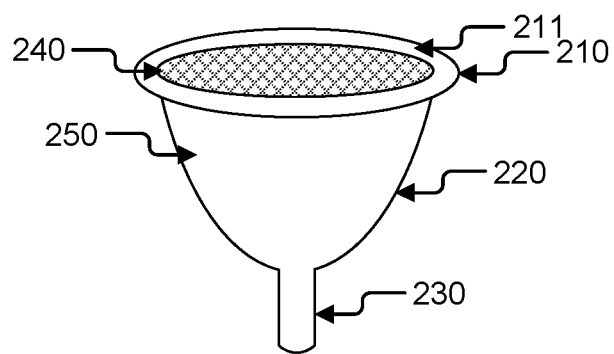
FIG. 2B illustrates an exemplary conception facilitating device comprising at least one cover, in accordance with some embodiments of the present disclosure.
Figure 2C:
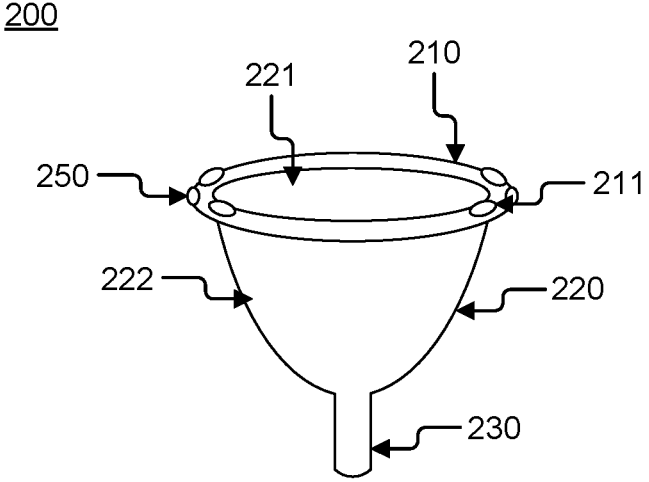
FIG. 2C illustrates an exemplary conception facilitating device comprising one or more ridges, in accordance with some embodiments of the present disclosure.

Referring now to FIGS. 2A, 2B, and 2C, an exemplary conception facilitating device 200, in accordance with some embodiments of the present disclosure, is illustrated. In some aspects, a conception facilitating device 200 may comprise at least one frame 210 and at least one base 220, wherein the at least one frame 210 may comprise at least one wall 211, and at least one base 220, wherein the at least one base may comprise at least one outer surface 222 and at least one inner surface 221. In some embodiments, the at least one frame 210 may be configured to at least partially surround the at least one base 220.

By way of example and not limitation, the conception facilitating device 200 may increase the likelihood of conception for a user when the at least one base 220 blocks at least an amount of ejaculate from existing the vaginal canal through the vaginal opening. In some embodiments, the conception facilitating device 200 may comprise at least one protruding member 230, wherein the at least one protruding member 230 may be configured to facilitate insertion and removal of the conception facilitating device 200, and wherein the at least protruding member 230 is at least partially attached to the at least one base 220. By way of example and not limitation, the at least one frame 210 may completely surround the at least one base 220, wherein the at least one frame 210 may comprise a circular configuration.

In some aspects, the at least one base 220 may comprise one or more curvatures. As a non-limiting example, the one or more curvatures may comprise a cup-like shape. In some aspects, a cup-like shape may be a receptacle that may comprise an inner wall, an outer wall, an enclosed bottom portion, an open top portion, wherein the diameter of the receptacle decreases in size the closer the diameter reaches the enclosed bottom portion.

As an illustrative example, the at least one frame 210 may completely surround the at least one base 220, wherein the at least one base may comprise a cup-like shape. In some embodiments, the at least one frame 210 may comprise a lip, wherein the lip may surround the at least one base 220. By way of example and not limitation, the lip may aid in blocking at least an amount of ejaculate from exiting the virginal canal through the vaginal opening.

In some embodiments, the conception facilitating device 200 may be configured 200 to comprise at least one cover 240, wherein the at least one cover 240 may be configured to enclose at least a portion of the at least one base 220. In some aspects, the at least one cover 240 may completely enclose the at least one base 220. In some embodiments, the at least one cover 240 may be at least partially connected to the at least one frame 210. In some aspects, the at least one cover 240 may completely attach to the at least one frame 210.

In some implementations, the at least one cover 240 may be removably attached to the at least one frame 210. In some aspects, the at least one cover 240 may comprise a sealed cover, such as an adhesive, as a non-limiting example. By way of example and not limitation, the at least one cover 240 may be configured to dissolve after a period of time or upon the happening of an event, such as being inserted into the vaginal opening. This may allow users to store at least an amount of ejaculate within the conception facilitating device 200 for a period of time before insertion. This may be useful for same sex couples who may need to store the ejaculate for a period of time.

By way of example and not limitation, the at least one cover 240 may comprise a dissolvable material. In some aspects, the at least one cover 240 may be configured to dissolve in response to the natural environment of the vaginal canal, such as the temperature, moisture, or pH levels. In some embodiments, the at least one cover 240 may be configured to contain at least an amount of ejaculate. As an illustrative example, a user may fill the at least one base 220 of the conception facilitating device 200 with at least an amount of ejaculate, and the user my store the at least an amount of ejaculate within the at least one base 220 by covering the at least one base 220 with at least one cover 240.

As an illustrative example, the at least one cover 240 may be configured to release different amounts of ejaculate over a period of time. The user may insert the covered, ejaculate-filled conception facilitating device into the vaginal canal, wherein the cover is configured to dissolve in the vaginal canal. The user may store the at least amount of ejaculate in the covered conception facilitating device for a period of time before insertion. This may be beneficial for users who do not engage in intercourse or for users who do not have immediate access to newly produced ejaculate, such as same-sex couples.

In some embodiments, the conception facilitating device 200 may comprise one or more ridges 250. As a non-limiting example, the one or more ridges 250 may be located on the edge of the at least one frame 210. In some embodiments, the one or more ridges 250 may be configured to hold the conception facilitating device 200 in place in the vaginal canal. As an illustrative example, the one or more ridges 250 may create traction between the conception facilitating device 200 and the vaginal wall, wherein the traction may at least partially limit the conception facilitating device from moving out of place. In some aspects, the one or more ridges 250 may be configured to direct at least an amount of ejaculate toward the cervix.

Figure 3A:
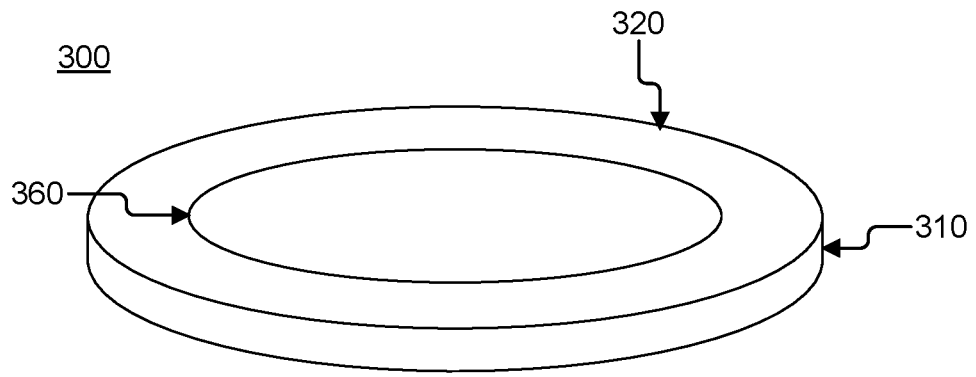
FIG. 3A illustrates a perspective view of an exemplary conception facilitating device, in accordance with some embodiments of the present disclosure.
Figure 3B:
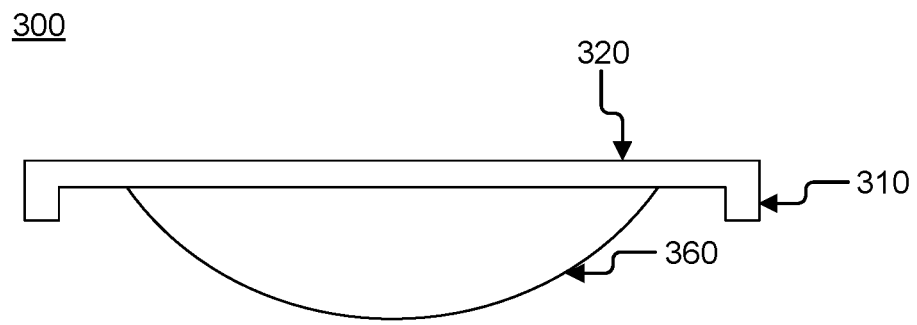
FIG. 3B illustrates a side view of an exemplary conception facilitating device, in accordance with some embodiments of the present disclosure.
Figure 3C:
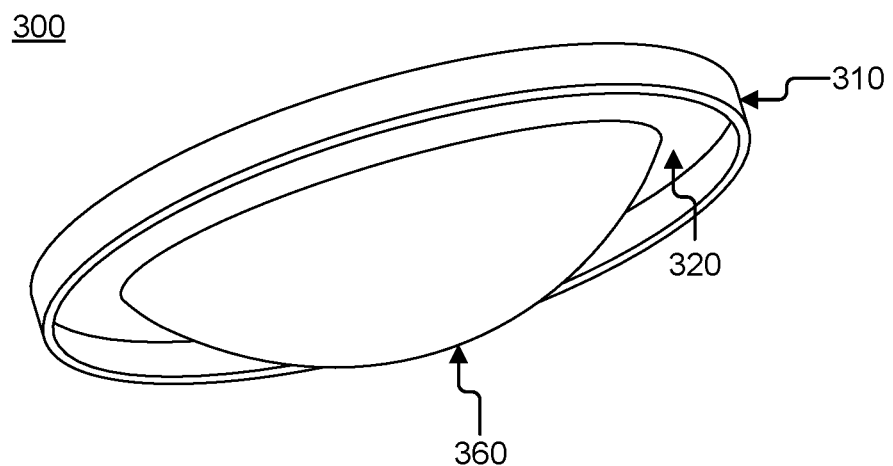
FIG. 3C illustrates a perspective view of an exemplary conception facilitating device, in accordance with some embodiments of the present disclosure.

Referring now to FIGS. 3A, 3B, and 3C, an exemplary conception facilitating device 300, in accordance with some embodiments of the present disclosure, are illustrated. In some aspects, a conception facilitating device 300 may comprise at least one frame 310 and at least one base 320. In some embodiments, the at least one frame 310 may be configured to at least partially surround the at least one base 320. In some embodiments, the at least one base 320 may be planar. In some aspects, the at least one base 320 may be configured to be located directly adjacent to at least a portion of the vaginal canal, wherein the connection may facilitate the blocking of an amount of ejaculate from exiting the vaginal canal through the vaginal opening. By way of example and not limitation, the at least one frame 320 may completely surround the at least one base 320, wherein the at least one frame 310 may comprise a lip that surrounds the at least one base 320. In some aspects, the at least one frame 310 that may comprise a lip may be configured to be located directly adjacent to at least a portion of the vaginal canal, wherein the connection may facilitate the blocking of an amount of ejaculate from exiting the vaginal canal through the vaginal opening. This prevention may aid in the facilitating of conception, which may take years for some users to conceive without such an aid.

In some embodiments, the conception facilitating device 300 may comprise at least one receptacle 360, wherein the at least one receptacle 360 may be configured to project at least an amount of ejaculate in the direction of the cervix. As a non-limiting example, the at least one receptacle 360 may comprise one or more materials to facilitate the projection of the at least an amount of ejaculate. As an illustrative example, a user may pull at least a portion of the receptacle 360 towards the vaginal opening, creating a buildup of potential energy. In some aspects, the receptacle 360 may comprise a flexible material, such as elastic. The user may then release the receptacle 360, which may project the at least an amount of ejaculate towards a user's cervix, which may increase the contact time between the ejaculate and a user's cervix. In some aspects, this increase in the contact time between the ejaculate and a user's cervix may increase the possibility of conception.

In some embodiments, the at least one receptacle 360 may comprise a rigid material. As a non-limiting example, the at least one receptacle 360 may be configured to hold at least an amount of ejaculate. In some aspects, the at least one receptacle 360 may be configured to be covered by a dissolvable material. As an illustrative example, the covered at least one receptacle 360 may hold at least an amount of ejaculate before insertion. By way of example and not limitation, the at least one cover may be configured to dissolve after a period of time or upon the happening of an event, such as being inserted into the vaginal opening. This may allow users to store an amount of ejaculate within the conception facilitating device 300 for a period of time before insertion. This may be useful for same sex couples who may need to store the ejaculate for a period of time.

Figure 4A:
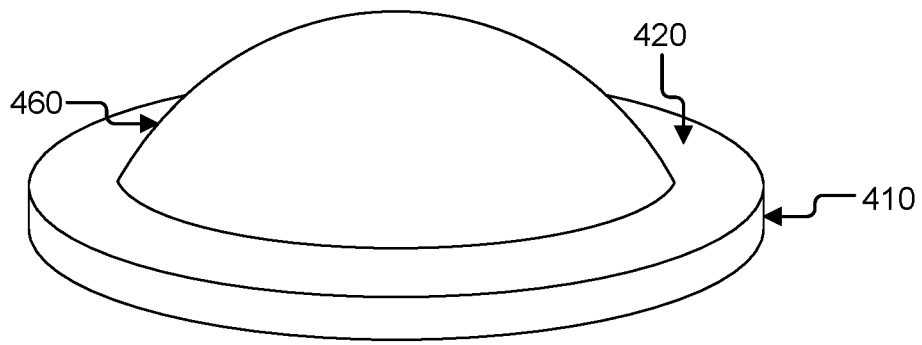
FIG. 4A illustrates a perspective view of an exemplary conception facilitating device, in accordance with some embodiments of the present disclosure.
Figure 4B:
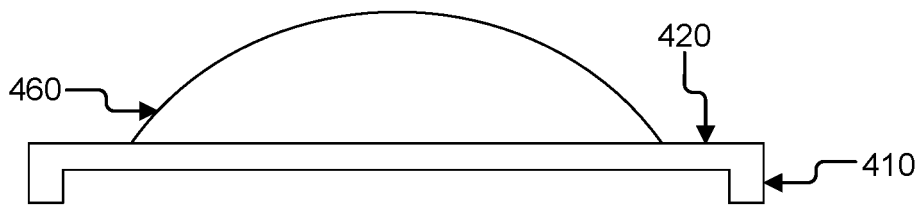
FIG. 4B illustrates a side view of an exemplary conception facilitating device, in accordance with some embodiments of the present disclosure.
Figure 4C:
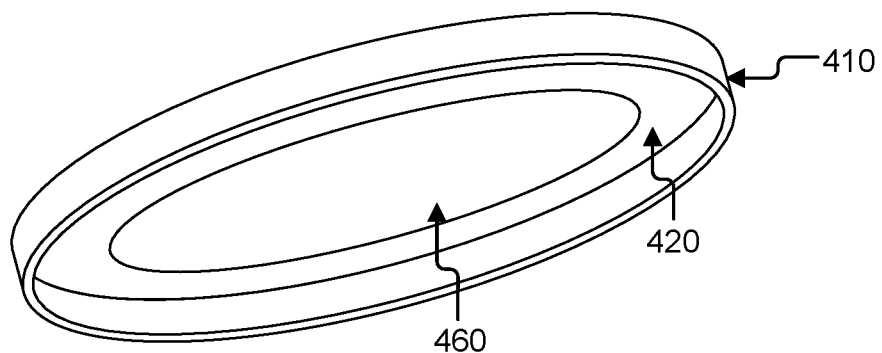
FIG. 4C illustrates a perspective view of an exemplary conception facilitating device, in accordance with some embodiments of the present disclosure.

Referring now to FIGS. 4A, 4B, and 4C, an exemplary conception facilitating device 400, in accordance with some embodiments of the present disclosure, are illustrated. In some aspects, a conception facilitating device 400 may comprise at least one frame 410 and at least one base 420. In some embodiments, the at least one frame 410 may be configured to at least partially surround the at least one base 420. In some embodiments, the at least one base 420 may be planar. By way of example and not limitation, the at least one base 420 may comprise a convex dome-shaped structure 460. In some aspects, the dome-shaped structure 460 may be configured to decrease the distance between the at least an amount of ejaculate and a user's cervix. In some aspects, the reduced distance between the at least an amount of ejaculate and the cervix may increase the possibility of conception.

Figure 5:
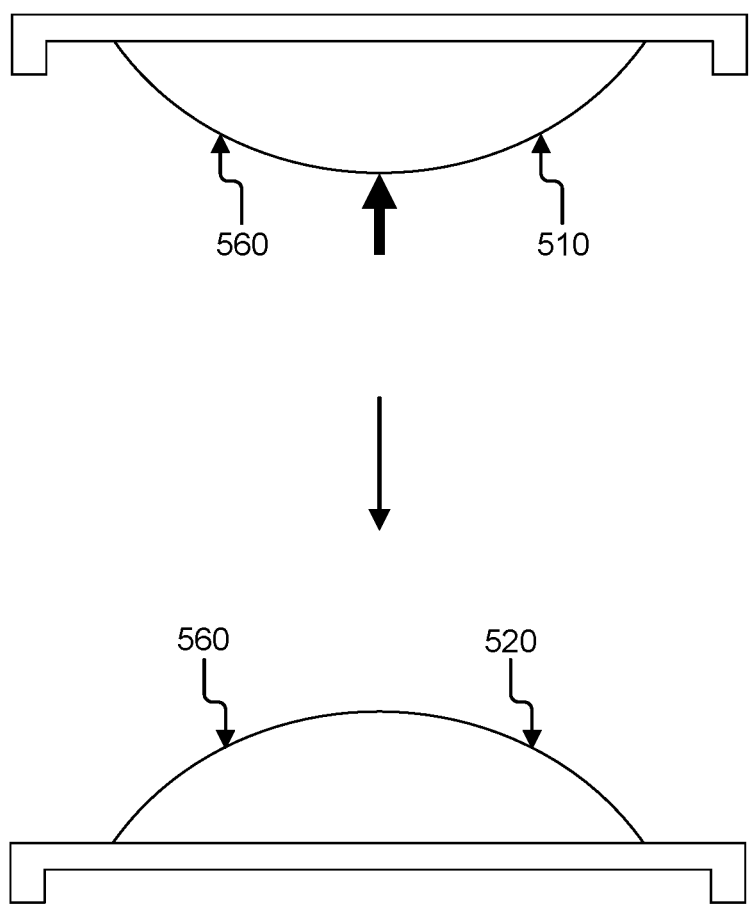
FIG. 5 illustrates an exemplary conception facilitating device, in accordance with some embodiments of the present disclosure.

Referring now to FIG. 5 an exemplary conception facilitating device 500, in accordance with some embodiments of the present disclosure, is illustrated. In some aspects, the conception facilitating device 500 may comprise at least one receptacle 560. In some embodiments, the at least one receptacle 560 may be configured to transition from a first position to a second position wherein the at least one receptacle 560 comprises a material that structurally biases the at least one receptacle 560 to the second position.

As a non-limiting example, a user may apply force the at least one receptacle 560 in the concave position 510 to invert the receptacle 560 into a convex position 520, wherein applying force may physically move the receptacle 560 beyond a threshold position. In some aspects, applying force may cause the receptacle 560 to fully transition into the structurally biased position. In some aspects, the at least one receptacle 560 may be in a first position of concave when inserting into the vaginal canal through the vaginal opening, and after insertion, a user may push the at least one receptacle 560 toward the cervix, which may cause the receptacle 560 to invert to a second position of convex. In some aspects, this second position may comprise the bottom of the receptacle 560 being located closer to the cervix.

In some embodiments, the at least one receptacle 560 may comprise a material configured to be manipulated into a position and stay in said position, such as plastic, rubber, or any polymer-based material, as non-limiting examples. In some aspects, the manipulation of the at least one receptacle 560 with project at least an amount of ejaculate toward the cervix, wherein the projection may increase the possibility of conception by increasing the connection between the ejaculate and the cervix.

Figure 6A:
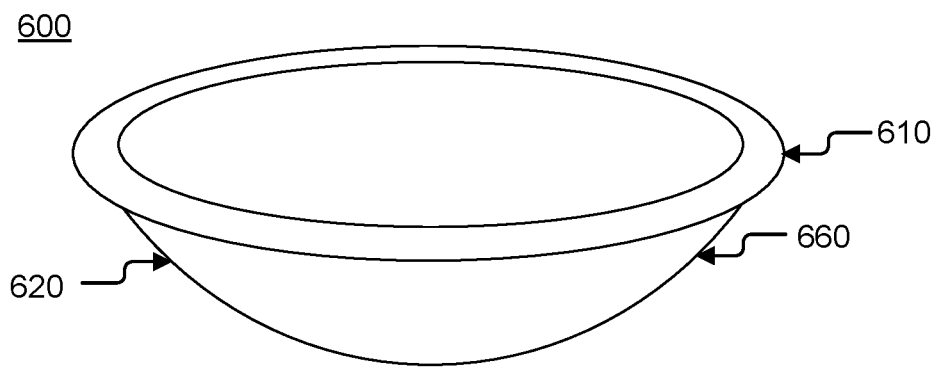
FIG. 6A illustrates a perspective view of an exemplary conception facilitating device, in accordance with some embodiments of the present disclosure.
Figure 6B:
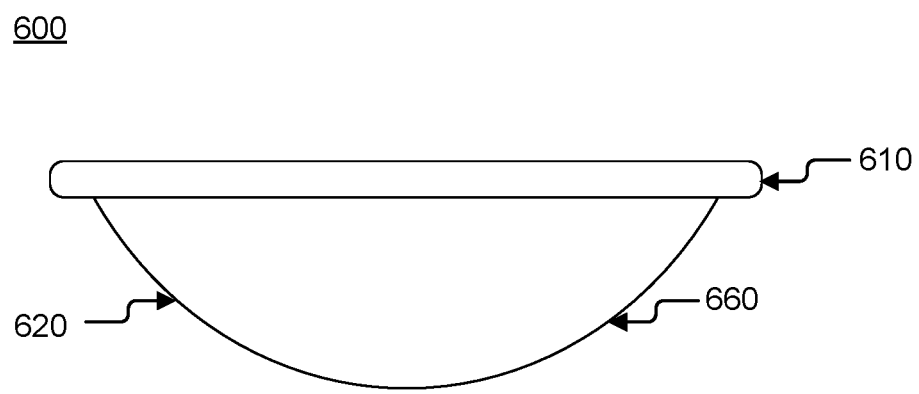
FIG. 6B illustrates a side view of an exemplary conception facilitating device, in accordance with some embodiments of the present disclosure.

Referring now to FIGS. 6A and 6B, an exemplary conception facilitating device 600, in accordance with some embodiments of the present disclosure, are illustrated. In some aspects, a conception facilitating device 600 may comprise at least one frame 610 and at least one base 620. In some embodiments, the at least one frame 610 may be configured to at least partially surround the at least one base 620. In some embodiments, the conception facilitating device 600 may comprise at least one receptacle 660, wherein the at least one receptacle 660 may be configured to hold at least an amount of ejaculate.

In some embodiments, the at least one base 620 may be planar. In some aspects, the conception facilitating device 600 may be insertable into a vaginal canal through the vaginal opening, wherein when the conception facilitating device 600 is inserted into the vaginal canal through the vaginal opening, at least one portion of the outer surface of the at least one base 620 may be directly adjacent to at least a portion of the vaginal canal. As a non-limiting example, the at least one base may limit the exiting of the amount of ejaculate from the vaginal opening by blocking the entrance to the vaginal opening. In some aspects, the conception facilitating device 600 may act as a plug to limit the exiting of the amount of ejaculate.

Figure 7:
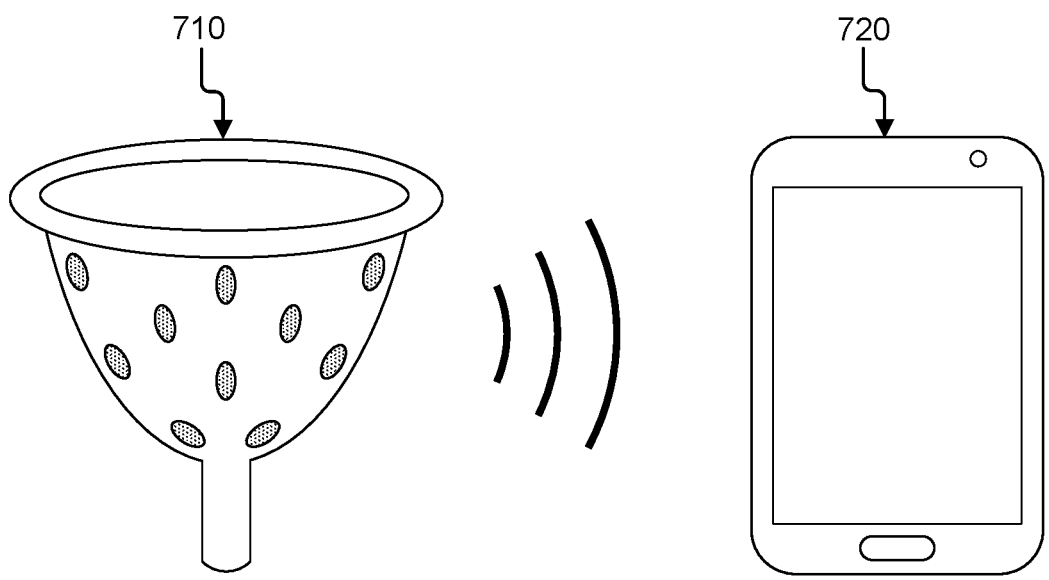
FIG. 7 illustrates an exemplary system for facilitating conception, in accordance with some embodiments of the present disclosure.

Referring now to FIG. 7, an exemplary conception facilitating device 700, in accordance with some embodiments of the present disclosure, is illustrated. In some aspects, the conception facilitating device 700 may comprise at least one transmitter and at least one sensor 710, wherein the at least one transmitter and at least one sensor 710 may be configured to interface with at least one external computing device 720. In some embodiments, the at least one sensor 710 may be configured to collect at least one datum, wherein the at least one datum may comprise time, pH, moisture levels, or any other health factor that may contribute to the health and wellness of the user. This may allow for the conception facilitating device 700 to gather information that could potentially instruct the user on best practices for conceiving, which can be a long and difficult process. For example, the conception facilitating device 700 may gather data that indicates the best time for a user to conceive.

In some aspects, the at least one database may be configured to store the at least one datum collected from the at least one sensor 710. This may allow for the collection of data overtime, which may be analyzed by the external computing device 720 to give the instructions to the user for facilitating conception. In some aspects, the at least one transmitter may transmit the at least one datum gathered from the at least one sensor 710 to at least one external computing device.

In some aspects, the at least one external device computing device may comprise a mobile device, wherein a user can access data gathered from the conception facilitating device 700 and the at external computing device 720 may analyze the data to give the user information about facilitating conception. In some aspects, the computing device 720 may comprise a display screen, wherein a user can interact with a graphical user interface. In some aspects, the graphical user interface may be configured to display data gathered from the at least one sensor 710, and display health recommendations. This may allow a user to make a decision that may aid in facilitating conception, and a user may use this data to consult with their physician about their health or their attempts to conceive. In some embodiments, the computing device 720 may comprise software to monitor the data gathered from the sensors to predict potential health concerns of the user.

In some aspects, the conception facilitating device 700 may comprise a timer. As a non-limiting example, the computing device 720 may notify a user when it is time to remove the conception facilitating device. In some embodiments, the conception facilitating device 700 may comprise a time release mechanism, wherein an amount of ejaculate may be released from the conception facilitating device 700 at a specific time indicated by the time release mechanism. As an example, an amount of ejaculate may be confined in the conception facilitating device 700 by a cover, and the cover may be configured to dissolved after a specified time. In some aspects, the conception facilitating device 700 may comprise one or more pulse electrodes to produce waves or signals that guide ejaculate toward a user's cervix.

As an example, one or more electrodes may produce waves or signals toward a user's cervix, which may guide the ejaculation toward a user's cervix. By increasing contact of the ejaculate with a user's cervix, the likelihood of conception may increase. In some aspects, the conception facilitating device 700 may comprise one or more electrodes to strengthen the vaginal canal. As a non-limiting example, a stronger vaginal canal may increase the possibility of conception.

In some aspects, the computing device 720 may comprise a graphical user interface (GUI). In some embodiments, a user may interface with medical professionals via the computing device 720, and the medical professionals may give advice based on the data gathered from the sensors. This may allow a user to identify potential behavior they can change to increase the possibility of conception.

Figure 8A:
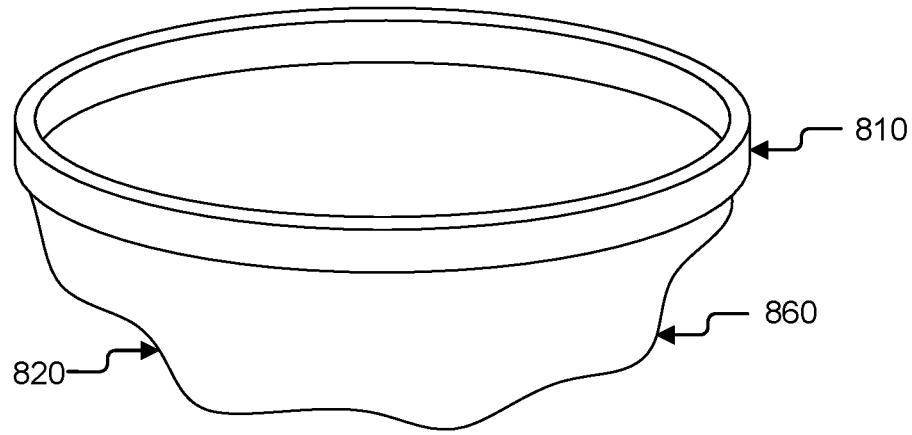
FIG. 8A illustrates a perspective view of an exemplary conception facilitating device, in accordance with some embodiments of the present disclosure.
Figure 8B:
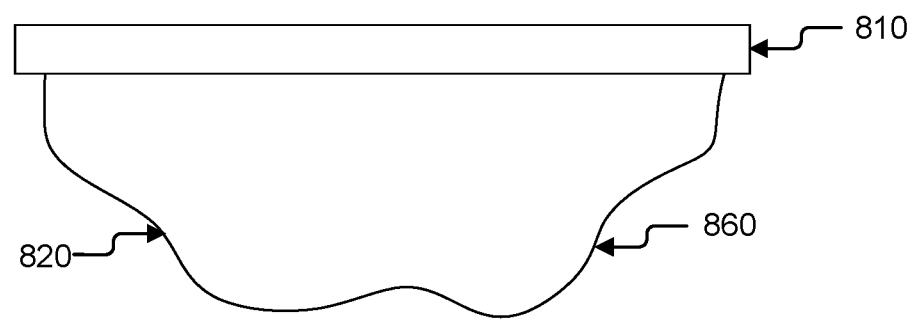
FIG. 8B illustrates a side view of an exemplary conception facilitating device, in accordance with some embodiments of the present disclosure.

Referring now to FIGS. 8A and 8B, an exemplary conception facilitating device 800, in accordance with some embodiments of the present disclosure, is illustrated. In some aspects, a conception facilitating device 800 may comprise at least one frame 810 and at least one base 820. In some embodiments, the at least one frame 810 may be configured to at least partially surround the at least one base 820. In some implementations, the conception facilitating device 800 may comprise at least one receptacle 860, wherein the at least one receptacle 860 may be configured to hold at least an amount of ejaculate. In some aspects, the at least one receptacle 860 may at least partially comprise at least one malleable material, such as cellophane, plastic, or silicone, as non-limiting examples, as well as any combination thereof. In some aspects, the conception facilitating device 800 may be configured to be disposable. By way of example and not limitation, a user of the conception facilitating device 800 may dispose of the conception facilitating device 800 after one or more uses. This may allow the user to use a new fresh conception facilitating device 800 for every attempt to conceive, which may be more convenient for some users.

In some embodiments, the at least one base 820 may comprise at least one substantially planar portion. In some aspects, the conception facilitating device 800 may be insertable into a vaginal canal through the vaginal opening, wherein when the conception facilitating device 800 is inserted into the vaginal canal through the vaginal opening, at least one portion of the outer surface of the at least one base 820 may be directly adjacent to and physically contact at least a portion of the vaginal canal. As a non-limiting example, the at least one base may limit the exiting of the amount of ejaculate from the vaginal opening by blocking the entrance to the vaginal opening. In some aspects, the conception facilitating device 800 may act as a plug to limit the exiting of the amount of ejaculate.

Figure 9:
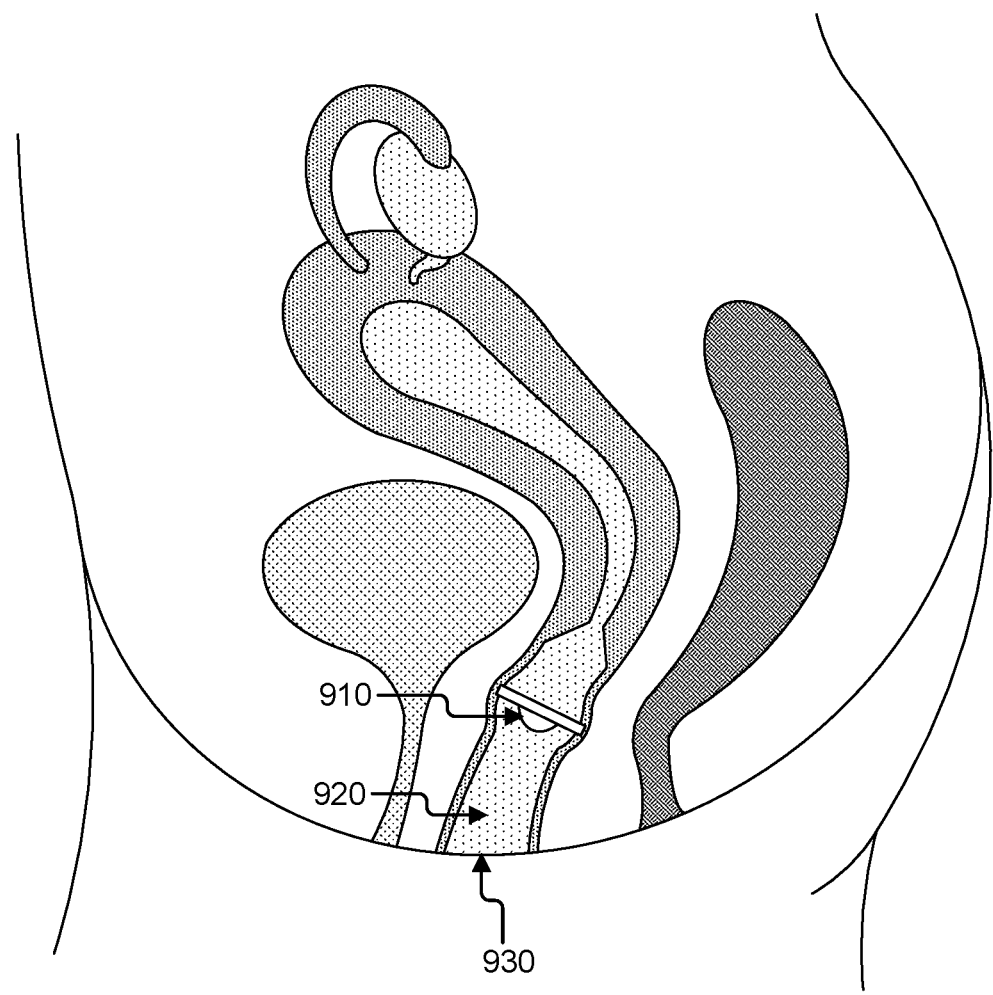
FIG. 9 illustrates an exemplary application of a conception facilitating device, in accordance with some embodiments of the present disclosure.

Referring now to FIG. 9, an exemplary application 900 of a conception facilitating device, in accordance with some embodiments of the present disclosure, is illustrated. In some aspects, the conception facilitating device 910 may be inserted into the vaginal canal 920 through the vaginal opening 930. In some aspects, the conception facilitating device may be insertable into a vaginal canal through the vaginal opening, wherein when the conception facilitating device may be inserted into the vaginal canal 920 through the vaginal opening 930, at least one portion of the outer surface of the at least one base 910 may be directly adjacent to at least a portion of the vaginal canal 920. In some embodiments, the conception facilitating device may be configured to block at least an amount of ejaculate from exiting a vaginal opening 930 from the vaginal canal 920.

As a non-limiting example, the conception facilitating device 910 may be manipulated to obtain a smaller configuration to fit into the vaginal opening 930, such as bending, compressing, or squeezing the conception facilitating device 910. In some aspects, the conception facilitating device 900 may be positioned at any location or in any orientation within the vaginal canal that effectively limits at least an amount of ejaculate from exciting the vaginal opening. In some embodiments, the conception facilitating device 910 may not create any suction on the cervix.

Figure 10:
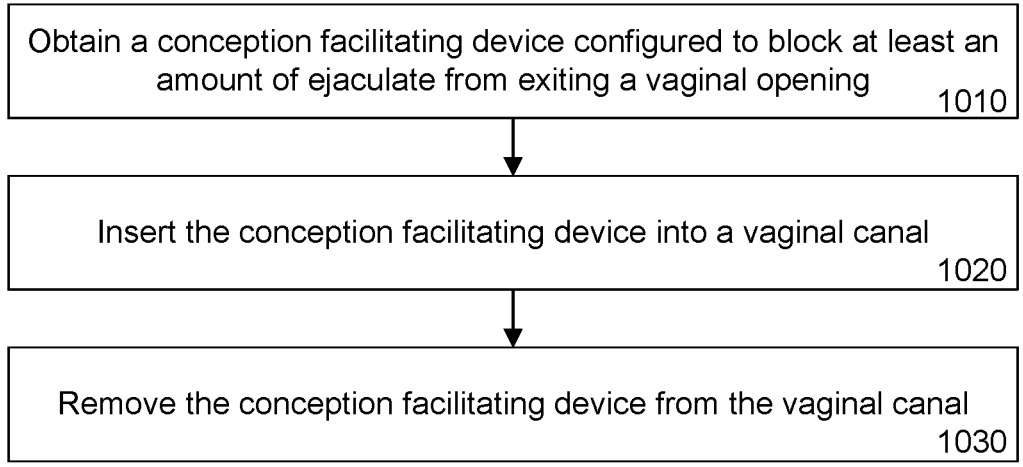
FIG. 10 illustrates an exemplary method for facilitating conception, in accordance with some embodiments of the present disclosure.

Referring now to FIG. 10 an exemplary method 1000 for facilitating conception, in accordance with some embodiments of the present disclosure is illustrated. At 1010, the method 1000 method for facilitating conception may comprise the step of obtaining a conception facilitating device configured wherein a conception facilitating device may comprise at least one frame and at least one base. In some aspects, the at least one frame may comprise at least one wall, and the at least one base may comprise at least one outer surface and at least one inner surface.

In some embodiments, the conception facilitating device may be configured to block at least an amount of ejaculate from exiting a vaginal opening. At 1020, the method 1000 may comprise the step of inserting the conception facilitating device into a vaginal canal through the vaginal opening so that it may be positioned relatively close to the vaginal opening. At 1030, the method 1000 may comprise removing the conception facilitating device from the vaginal canal. In some aspects, the conception facilitating device may be removed after a predetermined period of time.

As a non-limiting example, the conception facilitating device may be inserted into the vaginal canal after intercourse. As an additional non-limiting example, the method 1000 for facilitating conception may further comprise delivering at least an amount of ejaculate to the at least one base of the conception facilitating device before insertion into the vaginal canal, wherein the conception facilitating device may be inserted into the vaginal canal with the at least an amount of ejaculate.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single product or packaged into multiple products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A conception facilitating device comprising:
   at least one frame;
      wherein the at least one frame comprises at least one wall; and
   at least one base,
      wherein the at least one base comprises at least one outer surface, and at least one inner surface, and wherein the at least one frame at least partially surrounds the at least one base;
   wherein the conception facilitating device is insertable into a vaginal canal through a vaginal opening,
   wherein when the conception facilitating device is inserted into the vaginal canal through the vaginal opening, at least one portion of the at least one outer surface of the at least one base is directly adjacent to at least one portion of the vaginal canal,
   wherein the conception facilitating device is configured to block at least an amount of ejaculate from exiting the vaginal opening from the vaginal canal,
   wherein the at least one base comprises at least one receptacle,
   wherein manipulation of the at least one receptacle is configured to project at least a portion of the at least an amount of ejaculate in a direction toward a cervix within the vaginal canal,
   wherein the at least one receptacle is configured to transition from a first position to a second position,
   wherein the at least one receptacle comprises a material that structurally biases the at least one receptacle to the second position,
   wherein the first position comprises a concave configuration of the at least one receptacle, and
   wherein the second position comprises a convex configuration of the at least one receptacle.

2. The conception facilitating device of claim 1, further comprising:
   at least one protruding member,
      wherein the at least one protruding member is configured to facilitate insertion and removal of the conception facilitating device, and wherein the at least one protruding member is attached to at least a portion of the at least one base.

3. The conception facilitating device of claim 1, wherein every portion of the at least one outer surface of the at least one base contacts the at least one portion of the vaginal canal.

4. The conception facilitating device of claim 1, wherein the at least one frame comprises a lip that projects upwardly from the at least one base.

5. The conception facilitating device of claim 1, wherein the at least one frame is configured to interface with at least one cover, wherein the at least one cover is configured to enclose at least a portion of the at least one base.

6. The conception facilitating device of claim 1, wherein the at least one frame comprises one or more ridges.

7. The conception facilitating device of claim 1, wherein the conception facilitating device is configured to interface with at least one computing device.

8. The conception facilitating device of claim 7, wherein the conception facilitating device comprises at least one sensor, wherein the at least one sensor is configured to collect at least one datum.

9. The conception facilitating device of claim 8, wherein the conception device comprises at least one transmitter, wherein the at least one transmitter is configured to transmit the at least one datum to the at least one computing device.

10. A method for facilitating conception comprising:
   obtaining a conception facilitating device configured to block at least an amount of ejaculate from exiting a vaginal opening, wherein the conception facilitating device comprises at least one frame, wherein the at least one frame comprises at least one wall, and at least one base, wherein the at least one base comprises at least one outer surface, at least one inner surface, and at least one receptacle, and wherein the at least one frame at least partially surrounds the at least one base;
   inserting the conception facilitating device into a vaginal canal through the vaginal opening so that the conception facilitating device is positioned proximate to the vaginal opening, wherein at least one portion of the at least one outer surface of the at least one base contacts at least one portion of the vaginal canal after insertion;
   manipulating the at least one receptacle, wherein manipulation of the at least one receptacle is configured to project at least a portion of the at least an amount of ejaculate in a direction toward a cervix within the vaginal canal, wherein the at least one receptacle is configured to transition from a first position to a second position, wherein the at least one receptacle comprises a material that structurally biases the at least one receptacle to the second position, wherein the first position comprises a concave configuration of the at least one receptacle, and wherein the second position comprises a convex configuration of the at least one receptacle; and
   removing the conception facilitating device from the vaginal canal.

11. The method for facilitating conception of claim 10, wherein the conception facilitating device is inserted into the vaginal canal after intercourse.

12. The method of facilitating conception of claim 10, wherein the method further comprises delivering at least an amount of ejaculate to the at least one base of the conception facilitating device before insertion into the vaginal canal through the vaginal opening.

13. The method for facilitating conception of claim 10, wherein the conception facilitating device further comprises at least one protruding member,
wherein the at least one protruding member is configured to facilitate insertion and removal of the conception facilitating device, and wherein the at least protruding member is at least partially attached to the at least one base.

14. The method for facilitating conception of claim 10, wherein removing the conception facilitating device from the vaginal canal occurs after a predetermined period of time.

\* \* \* \* \*